United States Patent
Han et al.

(10) Patent No.: US 10,049,461 B2
(45) Date of Patent: Aug. 14, 2018

(54) MOTION EVALUATION SYSTEM AND METHOD

(71) Applicant: Samsung Life Public Welfare Foundation, Seoul (KR)

(72) Inventors: Youngyih Han, Seoul (KR); Wonjoong Cheon, Gyeonggi-do (KR); Junsang Cho, Seoul (KR); Sunghwan Ahn, Seoul (KR); Dooho Choi, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 15/493,539

(22) Filed: Apr. 21, 2017

(65) Prior Publication Data
US 2017/0309033 A1   Oct. 26, 2017

(30) Foreign Application Priority Data
Apr. 22, 2016  (KR) .................. 10-2016-0049406

(51) Int. Cl.
*G06K 9/00*   (2006.01)
*G06T 7/246*   (2017.01)
(Continued)

(52) U.S. Cl.
CPC ............ *G06T 7/246* (2017.01); *A61B 6/5276* (2013.01); *G06T 7/73* (2017.01);
(Continued)

(58) Field of Classification Search
CPC ......... A61B 6/5276; G06T 7/246; G06T 7/73; G06T 2207/10004; G06T 2207/30204
See application file for complete search history.

(56) References Cited

U.S. PATENT DOCUMENTS 6,143,003 A * 11/2000 Cosman .............. A61B 6/0421
                                                      128/846
6,490,477 B1   12/2002 Zylka et al.
(Continued)

FOREIGN PATENT DOCUMENTS

EP   1192913 A1   4/2002
JP   4330181 B2   6/2009

OTHER PUBLICATIONS

Cheon, Wonjoong et al.: "New Quality Assurance Method Using Motion Tracking for 6D Robotic Couches", *Progress in Medical Physics*, vol. 26, Suppl. 1, Apr. 2015, p. iii and p. 14.
(Continued)

*Primary Examiner* — Shefali Goradia
(74) *Attorney, Agent, or Firm* — McCarter & English, LLP (57) ABSTRACT

A motion evaluation system includes a marker member including a body part having a first surface and a second surface parallel to the first surface, a reference indication part indicating a center of the first surface, and a plurality of markers arranged on the first surface to be spaced apart from the reference indication part. The marker member is arranged on an object such that the reference indication part is arranged at a reference point of a first coordinate system. A plurality of cameras generate coordinate images by respectively photographing the markers. A first coordinate calculator calculates first coordinate values of the markers in a first coordinate system by using separation distances of the markers and a first distance between the first surface and the second surface, the separation distances and the first distance being previously stored. A second coordinate calculator calculates second coordinate values of the markers in a second coordinate system by using the coordinate images generated by the cameras. A coordinate converter produces a conversion relationship between the first coordinate sys-
(Continued)

tem and the second coordinate system by using the first coordinate values and the second coordinate values of the markers, and converts second motion information in the second coordinate system corresponding to a motion of the object objected by using the cameras to first motion information in the first coordinate system.

20 Claims, 4 Drawing Sheets

(51) Int. Cl.
    *A61B 6/00*     (2006.01)
    *G06T 7/73*     (2017.01)
(52) U.S. Cl.
    CPC ............... *G06T 2207/10004* (2013.01); *G06T 2207/10048* (2013.01); *G06T 2207/30204* (2013.01)

(56) References Cited

U.S. PATENT DOCUMENTS

| | | | |
|---|---|---|---|
| 7,860,216 B2 * | 12/2010 | Jongen | A61N 5/1049 378/205 |
| 9,682,254 B2 * | 6/2017 | Balakin | A61N 5/1082 |
| 2008/0212737 A1 * | 9/2008 | D'Souza | A61N 5/1049 378/65 |
| 2017/0154864 A1 * | 6/2017 | Hayata | H01L 24/75 |

OTHER PUBLICATIONS

Cheon, Wonjoong et al.: "Total Geometric Accuracy Quality Assurance Method Using Motion Tracking for Proton beam therapy", Sungkyunkwan University, Thesis presentation given on Apr. 24, 2015.

* cited by examiner

MOTION EVALUATION SYSTEM AND METHOD

CROSS-REFERENCE TO RELATED APPLICATION

This application claims the benefit of Korean Patent Application No. 10-2016-0049406, filed on Apr. 22, 2016, in the Korean Intellectual Property Office, the disclosure of which is incorporated herein in its entirety by reference.

BACKGROUND

1. Field

One or more embodiments relate to a motion evaluation system and method.

2. Description of the Related Art

In recent years, with the development of medical devices and advances in medical technology, medical devices have become more advanced. For example, in the treatment of cancer, surgical treatment, medication, and/or radiation treatment have been the mainstream. However, recently, a particle beam treatment apparatus has been developed, whereby particle beams such as proton beams or carbon beams are irradiated to a subject for treatment thereof. The treatment with the particle beam treatment apparatus is characteristically non-invasive and allows a patient to recover quickly after being treated.

In the treatment by using the particle beam treatment apparatus, the treatment is performed based on the Bragg peak, which is a characteristic of the particles. When a couch on which a patient is laid is not located at an accurate position during treatment, an unexpected amount of radiation may be irradiated onto an organ of the patient and thus the organ may be damaged if the patient has high radiation sensitivity. Accordingly, the position of the couch used for the particle beam treatment needs to be precisely controlled.

In the related art, to evaluate the motion of a couch, graphic paper, laser, or a goniometer has been used. However, since the above methods depend on the visual determination of a person, these methods may give erroneous results and thus it may be practically difficult to evaluate the precise motion of a couch.

SUMMARY

One or more embodiments include a motion evaluation system and method, whereby the motion of an object such as a couch can be precisely evaluated by using a marker member.

Additional aspects will be set forth in part in the description which follows and, in part, will be apparent from the description, or may be learned by practice of the presented embodiments.

According to one or more embodiments, a motion evaluation system includes a marker member including a body part having a first surface and a second surface parallel to the first surface, a reference indication part indicating a center of the first surface, and a plurality of markers arranged on the first surface to be spaced apart from the reference indication part, wherein the marker member is arranged on an object such that the reference indication part is arranged at a reference point of a first coordinate system, a plurality of cameras configured to generate coordinate images by respectively photographing the plurality of markers, a first coordinate calculator configured to calculate first coordinate values of the plurality of markers in a first coordinate system by using separation distances of the plurality of markers and a first distance between the first surface and the second surface, the separation distances and the first distance being previously stored, a second coordinate calculator configured to calculate second coordinate values of the plurality of markers in a second coordinate system by using the coordinate images generated by the plurality of cameras, and a coordinate converter configured to produce a conversion relationship between the first coordinate system and the second coordinate system by using the first coordinate values and the second coordinate values of the plurality of markers, and to convert second motion information in the second coordinate system corresponding to a motion of the object objected by using the plurality of cameras to first motion information in the first coordinate system.

The motion evaluation system may further include a laser member indicating a reference point of the first coordinate system.

The marker member may include at least three markers.

The markers may include a first marker, a second marker, a third marker, and a fourth marker arranged on the first surface of the body part.

The first coordinate calculator may calculate a three-dimensional (3D) first coordinate value of the plurality of markers by using the first marker, the second marker, the third marker, and the fourth marker.

The first coordinate calculator may calculate a first-1 coordinate value, a first-2 coordinate value, a first-3 coordinate value, and a first-4 coordinate value respectively corresponding to the first marker, the second marker, the third marker, and the fourth marker and a first-5 coordinate value, a first-6 coordinate value, a first-7 coordinate value, and a first-8 coordinate value at positions respectively corresponding to the first marker, the second marker, the third marker, and the fourth marker on the second surface.

The second coordinate calculator may calculate a 3D second coordinate value of the plurality of markers by using the first marker to the fourth marker.

The second coordinate calculator may calculate a second-1 coordinate value, a second-2 coordinate value, a second-3 coordinate value, and a second-4 coordinate value of the first marker, the second marker, the third marker, and the fourth marker corresponding to the second coordinate system by using the coordinate images generated by the plurality of cameras, and calculate a second-5 coordinate value, a second-6 coordinate value, a second-6 coordinate value, and a second-8 coordinate value on the second surface at positions respectively corresponding to the first marker, the second marker, the third marker, and the fourth marker by using the previously stored separation distances of the plurality of markers and first distance, and the calculated second-1 coordinate value, the calculated second-2 coordinate value, the calculated second-3 coordinate value, and the calculated second-4 coordinate value.

The coordinate converter may produce a conversion matrix that defines a conversion relationship between the first coordinate system and the second coordinate system by generating a first matrix of the first-1 coordinate value, the first-2 coordinate value, the first-3 coordinate value, the first-4 coordinate value, the first-5 coordinate value, the first-6 coordinate value, the first-7 coordinate value, and the first-8 coordinate value, generating a second matrix of the second-1 coordinate value, the second-2 coordinate value, the second-3 coordinate value, the second-4 coordinate value, the second-5 coordinate value, the second-6 coordinate value, the second-7 coordinate value, and the second-8 coordinate value, calculating an inverse matrix of any one of the first matrix and the second matrix, and calculating the inverse matrix and the other one of the first matrix and the second matrix.

According to one or more embodiments, a motion evaluation method includes preparing a marker member on an object, the marker member comprising a body part having a first surface and a second surface parallel to the first surface, a reference indication part indicating a center of the first surface, and a plurality of markers arranged on the first surface to be spaced apart from the reference indication part, arranging a center of the first surface of the marker member at a reference point of a first coordinate system, calculating, by using a first coordinate calculator, first coordinate values of the plurality of markers in a first coordinate system by using separation distances of the plurality of markers and a first distance between the first surface and the second surface, the separation distances and the first distance being previously stored, generating, by using a plurality of cameras, coordinate images of a plurality of markers by photographing the plurality of markers, calculating, by using a second coordinate calculator, second coordinate values of the plurality of markers in a second coordinate system by using the coordinate images generated by the plurality of cameras, and producing a conversion relationship between the first coordinate system and the second coordinate system by using the first coordinate values and the second coordinate values of the plurality of markers.

The motion evaluation method may further include converting, by using the coordinate converter, second motion information in the second coordinate system corresponding to a motion of the object objected by using the plurality of cameras, to first motion information in the first coordinate system.

The motion evaluation method may further include indicating a reference point of the first coordinate system by using a laser member.

The marker member may include at least three markers.

The plurality of markers may include a first marker, a second marker, a third marker, and a fourth marker arranged on the first surface of the body part.

The calculating of the first coordinate value may include calculating a three-dimensional (3D) first coordinate value of the plurality of markers by using the first marker, the second marker, the third marker, and the fourth marker.

The calculating of the first coordinate value may include calculating a first-1 coordinate value to a first-4 coordinate value corresponding to the first marker, the second marker, the third marker, and the fourth marker, and calculating a first-5 coordinate value to a first-8 coordinate value at positions corresponding to the first marker, the second marker, the third marker, and the fourth marker on the second surface of the body part.

The calculating of the second coordinate valve may include calculating a 3D second coordinate value of the plurality of markers by using the first marker, the second marker, the third marker, and the fourth marker.

The calculating of the second coordinate value may include calculating a second-1 coordinate value to a second-4 coordinate value of the first marker to the fourth marker corresponding to the second coordinate system by using the coordinate images, and calculating a second-5 coordinate value to a second-8 coordinate value on the second surface of the body part at positions corresponding to the first marker to the fourth marker by using the previously stored separation distances of the plurality of markers and first distance, and the calculated second-1 coordinate value to second-4 coordinate value.

The producing of the conversion relationship may include generating a first matrix of the first-1 coordinate value to the first-8 coordinate value, generating a second matrix of the second-1 coordinate value to the second-8 coordinate value, calculating an inverse matrix of any one of the first matrix and the second matrix, and calculating the inverse matrix and the other one of the first matrix and the second matrix, thereby producing a conversion matrix defining a conversion relationship between the first coordinate system and the second coordinate system.

According to one or more embodiments, a non-transitory computer readable recording medium having recorded thereon a program, which when executed by a computer, performs the motion evaluation method, which includes preparing a marker member on an object, the marker member comprising a body part having a first surface and a second surface parallel to the first surface, a reference indication part indicating a center of the first surface, and a plurality of markers arranged on the first surface to be spaced apart from the reference indication part, arranging a center of the first surface of the marker member at a reference point of a first coordinate system, calculating, by using a first coordinate calculator, first coordinate values of the plurality of markers in a first coordinate system by using separation distances of the plurality of markers and a first distance between the first surface and the second surface, the separation distances and the first distance being previously stored, generating, by using a plurality of cameras, coordinate images of a plurality of markers by photographing the plurality of markers, calculating, by using a second coordinate calculator, second coordinate values of the plurality of markers in a second coordinate system by using the coordinate images generated by the plurality of cameras, and producing a conversion relationship between the first coordinate system and the second coordinate system by using the first coordinate values and the second coordinate values of the plurality of markers.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As the inventive concept allows for various changes and numerous embodiments, embodiments will be illustrated in the drawings and described in detail in the written description. However, this is not intended to limit the present inventive concept to particular modes of practice, and it is to be appreciated that all changes, equivalents, and substitutes that do not depart from the spirit and technical scope of the present inventive concept are encompassed in the present inventive concept. In the description of the present inventive concept, certain detailed explanations of the related art are omitted when it is deemed that they may unnecessarily obscure the essence of the inventive concept.

It will be understood that although the terms "first," "second," etc. may be used herein to describe various components, these components should not be limited by these terms. These components are only used to distinguish one component from another.

As used herein, the singular forms "a," "an" and the are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of components in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

In the present specification, when a layer, region, or component "connects" or is "connected" to another layer, region, or component, the layer, region, or component may contact or may be connected to the other layer, region, or component not only directly, but also electrically through at least one of other layer, region, or components interposed therebetween.

Figure 1:
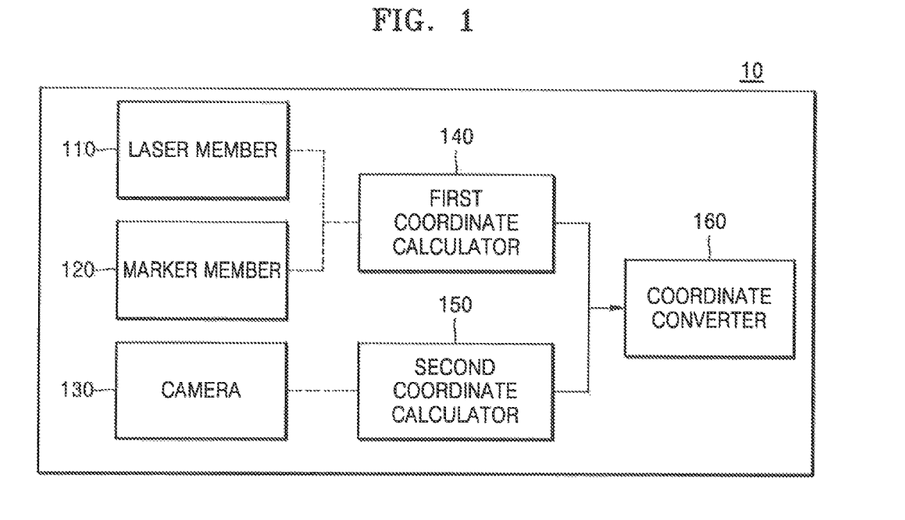
FIG. 1 is a schematic block diagram of a motion evaluation system according to an embodiment.
Figure 2:
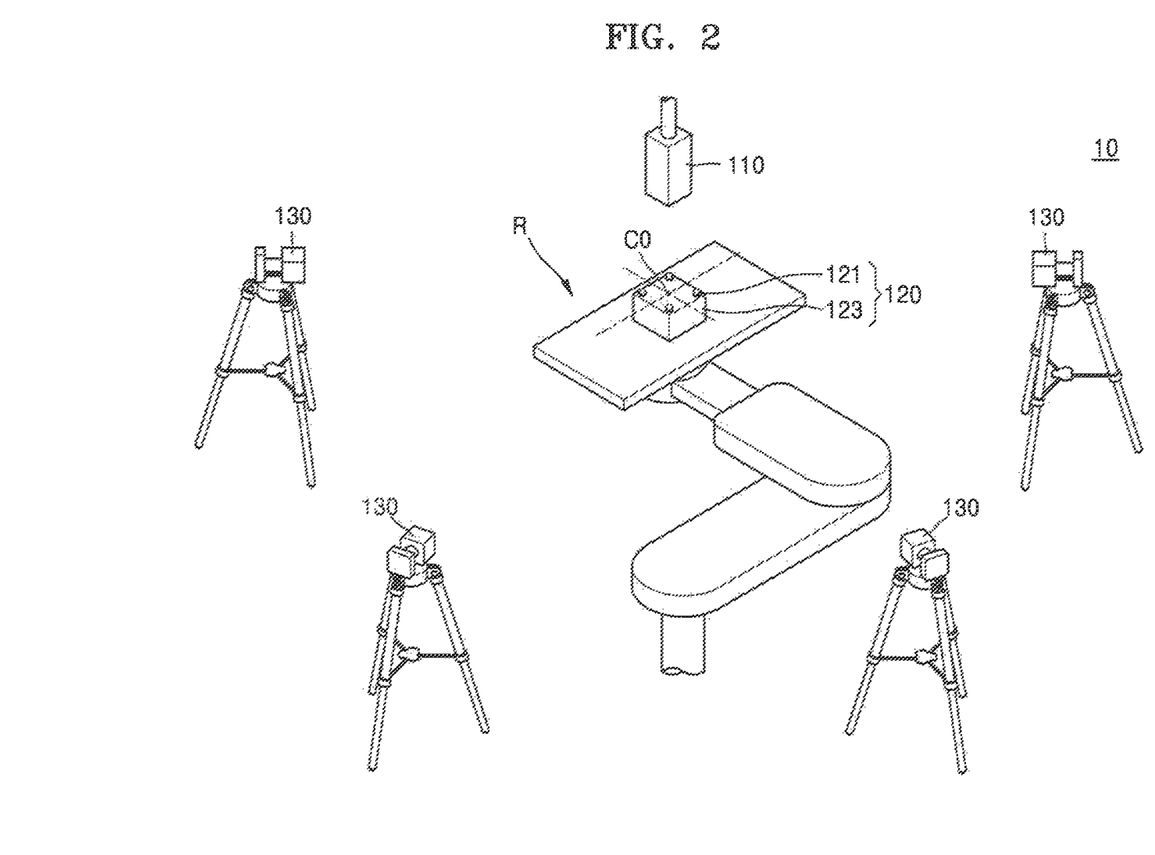
FIG. 2 schematically illustrates the motion evaluation system of FIG. 1 according to an embodiment.

FIG. 1 is a schematic block diagram of a motion evaluation system 10 according to an embodiment. FIG. 2 schematically illustrates the motion evaluation system 10 of FIG. 1 according to an embodiment.

Referring to FIGS. 1 and 2, the motion evaluation system 10 according to the present embodiment may include a laser member 110, a marker member 120, a plurality of cameras 130, a first coordinate calculator 140, a second coordinate calculator 150, and a coordinate converter 160.

The laser member 110 may indicate a reference point C0 of a first coordinate system by using a laser beam. The first coordinate system is a coordinate system of an object R. The object R may be a couch that can move. The coordinate system of the object R is the same as a three-dimensional (3D) coordinate system of a treatment room where the object R may be placed. The laser member 110, as illustrated in the drawings, may indicate the reference point C0 of the first coordinate system by irradiating a laser beam in a cross (+) shape.

The marker member 120 may be arranged on the object R that is movable. The marker member 120 may include a body part 123 having a first surface 123-1 (see FIG. 3) and a second surface 123-2 (see FIG. 3) parallel to the first surface 123-1, a reference indication part 125 indicating a center of the first surface 123-1, and a plurality of markers 121 arranged on the first surface 123-1 and spaced apart from the reference indication part 125. The markers 121 are infrared (IR) markers and may be of either a passive type or an active type. A passive type marker is formed of a material that reflects an IR ray irradiated from the outside. In this state, the cameras 130 may detect reflected light and generate a coordinate image. An active type marker may directly emit light such as an IR ray, and the cameras 130 may detect the light and generate a coordinate image. The present inventive concept is not limited regarding the marker type. However, in the following description, a passive type marker is described as an example for convenience of explanation.

The marker member 120 may include at least three markers 121 to obtain a 3D coordinate value. However, four or more markers may be included to increase the accuracy of evaluating a motion. In the present embodiment, use of four markers is described as an example.

Figure 3:
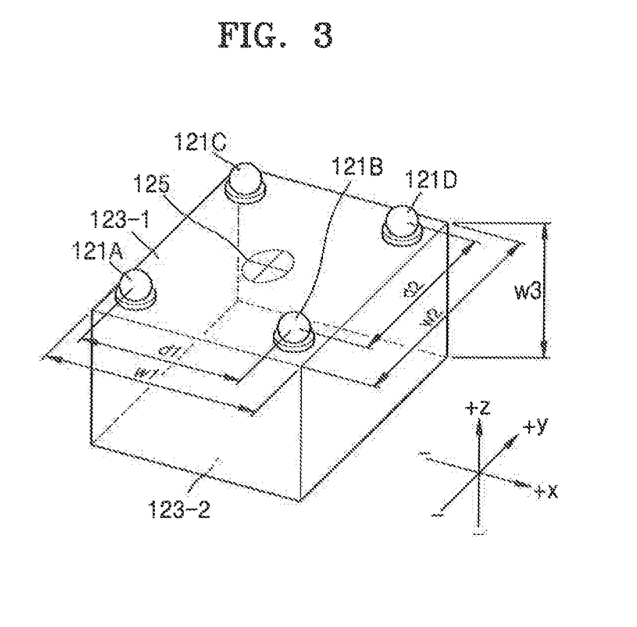
FIGS. 3 and 4 are perspective views schematically illustrating the relationship among a plurality of markers of the marker member of FIG. 2 according to an embodiment.
Figure 4:
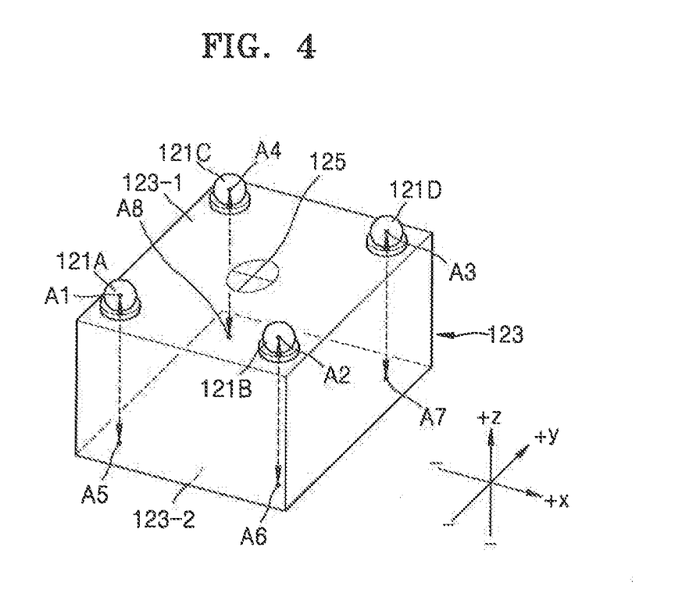

FIGS. 3 and 4 are perspective views schematically illustrating the relation between the markers 121 of the marker member 120 of FIG. 2.

Referring to FIG. 3, the marker member 120 may include the body part 123. The body part 123 may include the first surface 123-1 and the second surface 123-2 parallel to the first surface 123-1. For example, the body part 123 may be a cube or a cuboid having six faces, the adjacent faces meeting at 90 degrees with one another. Furthermore, lengths w1, w2, and w3 of the respective edges of the body part 123 are already known information, and the body part 123 may be formed of a material such that the lengths w1, w2, and w3 of the respective edges are not changed by external factors. In detail, a first distance w3, which is a distance between the first surface 123-1 and the second surface 123-2, may indicate a height from the object R to the markers 121.

The markers 121 may include a first marker 121A, a second marker 121B, a third marker 121C, and a fourth marker 121D, which are arranged on the first surface 123-1 of the body part 123. For example, the first marker 121A to the fourth marker 121D may be arranged adjacent to the respective corners of the first surface 123-1 of the body part 123. The distances between the markers 121, that is, a first separation distance d1 between the first marker 121A and the second marker 121B and a second separation distance d2 between the second marker 121B and the fourth marker 121D, are also already known information.

The marker member 120 may include the reference indication part 125 indicating the center of the first surface 123-1 of the body part 123. The reference indication part 125 may have a cross (+) shape and may be formed at an intersection of lines perpendicularly passing through center points of the respective edges.

Referring to FIGS. 1 to 4, the first coordinate calculator 140 may previously store the separation distances d1 and d2 between the markers 121 and the lengths w1, w2, and w3 of the respective edges of the body part 123, in detail, the first distance w3 between the first surface 123-1 and the second surface 123-2. The first coordinate calculator 140 may calculate first coordinate values of the markers 121 in the first coordinate system by using the previously stored separation distances d1 and d2 between the markers 121 and first distance w3. The first coordinate values may be a 3D first coordinate value of the markers 121.

In detail, the first coordinate calculator 140 may calculate a first-1 coordinate value A1, a first-2 coordinate value A2, a first-3 coordinate value A3, and a first-4 coordinate value A4 respectively corresponding to the first marker 121A, the second marker 121B, the third marker 121C, and the fourth marker 121D with respect to the reference point C0 of the first coordinate system. Furthermore, the first coordinate calculator 140 may calculate a first-5 coordinate value A5, a first-6 coordinate value A6, a first-7 coordinate value A7, and a first-8 coordinate value A8 on the second surface 123-2 at positions respectively corresponding to the first marker 121A, the second marker 121B, the third marker 121C, and the fourth marker 121D. In other words, the first coordinate calculator 140 may calculate eight (8) coordinate values in the first coordinate system by using the information of the marker member 120.

Referring back to FIGS. 1 and 2, the cameras 130 may generate coordinate images by photographing the markers 121 of the marker member 120. The cameras 130 may generate coordinate images of the markers 121 by photographing IR rays reflected from the markers 121 and returned to the cameras 130. Although not illustrated, an IR ray is irradiated by using an IR generator (not shown) and the irradiated IR ray is reflected from each of the markers 121. In an embodiment, a plurality of IR generators are installed in various directions to irradiate IR rays, and a circle is searched for by using a circle fitting method using the brightest pixels from the coordinate images photographed and generated by the markers 121, thereby identifying the positions of the markers 121 by obtaining a center coordinate of a found circle. However, the present disclosure is not limited thereto. In another embodiment, when the IR generators are arranged in various directions to irradiate IR rays, the center of the markers 121 shines the brightest. The cameras 130 find the position of the brightest pixel and thus the positions of the markers 121 may be identified. The second coordinate calculator 150 described later may calculate second coordinate values of the markers 121 in a second coordinate system through the above coordinate images. The number of cameras theoretically required to obtain a 3D second coordinate value is two. However, just an approximate 3D position may be identified by using only two cameras. Accordingly, at least three cameras are needed to identify an accurate 3D position. In FIG. 2, four cameras are illustrated as the cameras 130 for improvement the accuracy of identifying the 3D position.

The second coordinate calculator 150 may calculate second coordinate values in the second coordinate system of the markers 121 based on the coordinate images generated by the cameras 130. The second coordinate calculator may calculate a 3D second coordinate value of the markers 121 by using the first marker 121A, the second marker 121B, the third marker 121C, and the fourth marker 121D.

The second coordinate calculator 150 may calculate a second-1 coordinate value, a second-2 coordinate value, a second-3 coordinate value, and a second-4 coordinate value in the second coordinate system of the first marker 121A, the second marker 121B, the third marker 121C, and the fourth marker 121D by using the coordinate images generated by the cameras 130. The second coordinate calculator 150, like the first coordinate calculator 140, may previously store the separation distances d1 and d2 of the markers 121 and the lengths w1, w2, and w3 of the respective edges of the body part 123 including at least the first distance w3 between the first surface 123-1 and the second surface 123-2. Accordingly, the second coordinate calculator 150 may calculate a second-5 coordinate value, a second-6 coordinate value, a second-7 coordinate value, and a second-8 coordinate value on the second surface 123-2 at positions corresponding to the first marker 121A, the second marker 121B, the third marker 121C, and the fourth marker 121D. In other words, the second coordinate calculator 150 may calculate eight (8) second coordinate values in the second coordinate system.

The coordinate converter 160 may produce a conversion relationship between the first coordinate system and the second coordinate system by using the first coordinate values and the second coordinate values of the markers 121. The coordinate converter 160 may convert second motion information in the second coordinate system corresponding to a motion of the object R obtained by using the cameras 130 to first motion information in the first coordinate system.

According to an embodiment, the motion evaluation system 10 having the above structure may enable accurate location tracking of the object R by using the marker member 120 and the cameras 130. As the location is converted to the first coordinate system corresponding to a treatment room coordinate system, the motion of the object R may be accurately evaluated.

The method of evaluating a motion according to an embodiment is described in detail with reference to FIGS. 1 to 5.

Figure 5:
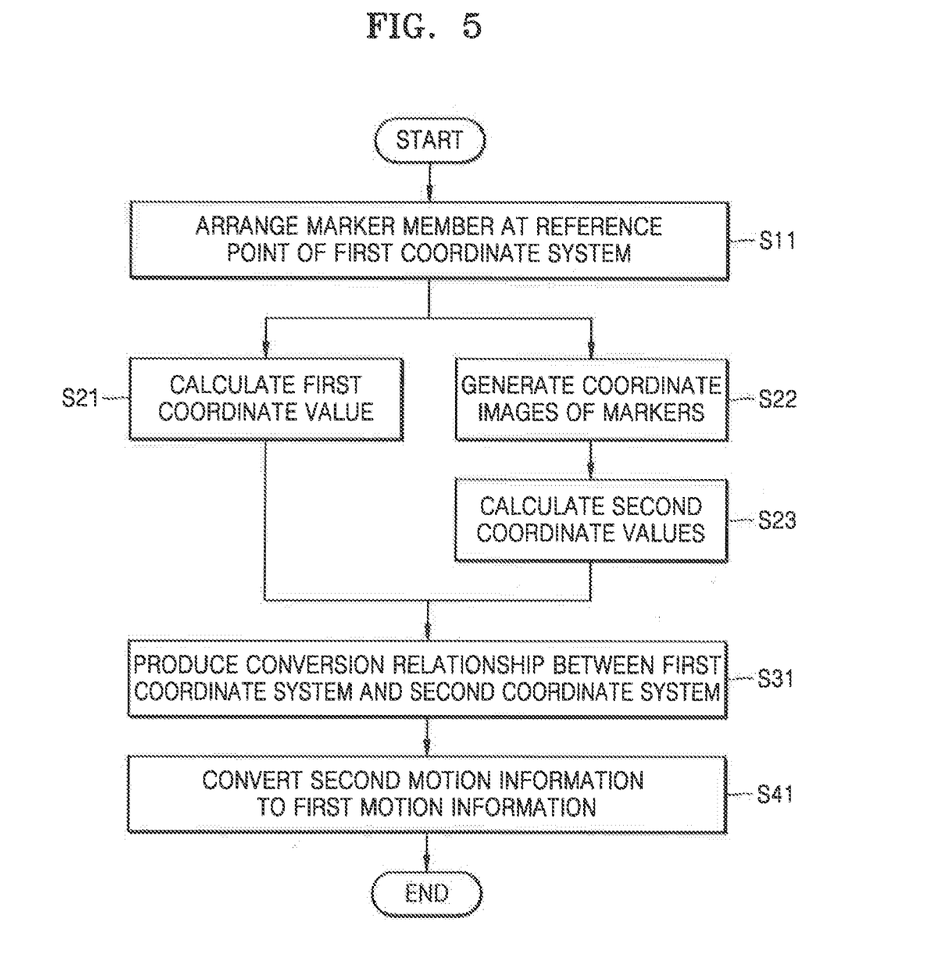
FIG. 5 is a flowchart for sequentially explaining a motion evaluation method according to an embodiment.

FIG. 5 is a flowchart for sequentially explaining a motion evaluation method according to an embodiment.

Referring to FIG. 5, according to the motion evaluation method according to the present embodiment, first, the marker member 120 including the body part 123 having the first surface 123-1 and the second surface 123-2 parallel to the first surface 123-1, the reference indication part 125 indicating the center of the first surface, and the markers 121 arranged on the first surface 123-1 and spaced apart from the reference indication part 125 is prepared on the object R.

Then, the center of the first surface 123-1 of the marker member 120 is arranged at the reference point C0 of the first coordinate system (S11). The reference point C0 of the first coordinate system is indicated by the laser member 110. Furthermore, since the marker member 120 includes the reference indication part 125 that indicates the center of the first surface 123-1 of the body part 123, the position of the marker member 120 may be determined by aligning the reference indication part 125 of the marker member 120 and the reference point C0 of the first coordinate system.

Next, the first coordinate values of the markers 121 in the first coordinate system are calculated by using the first coordinate calculator 140 (S21). The separation distances d1 and d2 of the markers 121 and the lengths w1 w2, and w3 of the respective edges of the body part 123 including at least the first distance w3 between the first surface 123-1 and the second surface 123-2 may be previously stored in the first coordinate calculator 140. A 3D first coordinate value of the markers 121 may be calculated by the first coordinate calculator 140 by using the separation distances d1 and d2 of the markers 121 and the first distance w3. For example, a first coordinate value of a reference point may be (0, 0, 0), a first-1 coordinate value of the first marker 121A may be (−d1/2, −d2/2, 0), and a first-5 coordinate value may be (−d1/2, −d2/2, −w3). Likewise, the other first coordinate values are calculated in the same manner, and thus a total eight (8) first coordinate values may be calculated.

Next, coordinate images are generated by photographing the markers 121 by using the cameras 130 (S22). A process of forming a virtual 3D coordinate is needed before the photographing of the markers 121 by using the cameras 130, which is referred to as calibration.

Calibration is needed for the following reasons. A 3D second coordinate system may be set to be within a range where the cameras 130 may capture images. The position (0, 0, 0) may be set by a user and to match the reference point C0 of the first coordinate system. A relationship between the 3D second coordinate system and the coordinated of each of the cameras 130 is obtained by calculating the distance and direction of each of the cameras 130 for photographing, and a distorted coordinate of a camera lens may be corrected. The lenses of the cameras 130 used by the motion evaluation method may include various lenses from a wide-angle lens (8 mm) to standard zoom lens, a single lens, and a telephoto lens. In the case of a wide-angle lens, since a distortion phenomenon occurs further from the center toward the periphery in a camera screen, the distortion phenomenon needs to be corrected by using a software algorithm. Since every lens is affected by the distortion phenomenon, an algorithm may be used to identify a degree of distortion of each lens and correct the distortion through calibration prior to measurement.

The calibration may be performed via various methods. For example, a T-shaped wand with already known specifications is previously measured and then coordinate calculation variables are corrected to match image information acquired by the cameras 130 with the specifications of the T-shaped wand. First, for dynamic calibration, the T-shaped wand may be moved so as to be properly photographed by all of the cameras 130. After the motion measurement, the T-shaped wand is placed at a position where the coordinate (0, 0, 0) is desired to be generated, thereby performing static calibration.

After the calibration process, coordinate images of the markers 121 may be generated by using the cameras 130.

Next, the second coordinate values of the markers 121 in the second coordinate system are calculated by the second coordinate calculator 150 by using the coordinate images (S23). First, the second coordinate calculator 150 may calculate the second-1 coordinate value, the second-2 coordinate value, the second-3 coordinate value, and the second-4 coordinate value in the second coordinate system of the first marker 121A, the second marker 121B, the third marker 121C, and the fourth marker 121D, by using the coordinate images. The second coordinate calculator 150 previously store the separation distances d1 and d2 of the markers 121 and the first distance w3, and the second-5 coordinate value, the second-6 coordinate value, the second-7 coordinate value, and the second-8 coordinate value on the second surface 123-2 at positions corresponding to the first marker 121A, the second marker 121B, the third marker 121O, and the fourth marker 121D may be calculated using the stored data (S23).

Next, a conversion relationship between the first coordinate system and the second coordinate system may be produced by the coordinate converter 160 by using the first coordinate values and the second coordinate values of the markers 121. In detail, the coordinate converter 160 generates a first matrix of the first-1 coordinate value A1, the first-2 coordinate value A2, the first-3 coordinate value A3, the first-4 coordinate value A4, the first-5 coordinate value A5, the first-6 coordinate value A6, the first-7 coordinate value A7, and the first-8 coordinate value A8. A first matrix R that represents the first coordinate system, that is, a treatment room coordinate system, may be expressed as [X, Y, Z, 1]T. Furthermore, the coordinate converter 160 generates a second matrix of the second-1 coordinate value, the second-2 coordinate value, the second-3 coordinate value, the second-4 coordinate value, the second-5 coordinate value, the second-6 coordinate value, the second-7 coordinate value, and the second-8 coordinate value. A second matrix V that represents the second coordinate system, that is, a camera coordinate system, may be expressed by [X, Y, Z, 1]T. Since each of the first matrix and the second matrix includes eight (8) coordinate values, each of the first matrix and the second matrix may be expressed by Equation 1. Furthermore, a correlationship between the first matrix and the second matrix may be defined by Equation 2.

$$V = [V_1 V_2 V_3 V_4 V_5 V_6 V_7 V_8]$$

$$R = [R_1 R_2 R_3 R_4 R_5 R_6 R_7 R_8] \quad \text{[Equation 1]}$$

$$R = TV \quad \text{[Equation 2]}$$

A conversion relationship may be produced by using the above correlationship. In other words, the coordinate converter 160 calculates an inverse matrix of any one of the first matrix and the second matrix and then calculates the inverse matrix and the other one of the first matrix and the second matrix, thereby producing a conversion matrix as expressed by Equation 3 (S31).

$$T = RV^{-1} \quad \text{[Equation 3]}$$

The size of each of the first matrix and the second matrix may be 4×8, and the size of a conversion matrix TVR may be 4×4.

Then, the second motion information in the second coordinate system corresponding to a motion of the object R obtained by using the cameras 130 may be converted to the first motion information in the first coordinate system by using the conversion relationship produced by the coordinate converter 160 (S41). In this regard, according to the motion evaluation method including the above-described operations, the motion of the object R may be accurately tracked and converted to the first coordinate system, that is, the treatment room coordinate system, and then provided for use. Thus, the motion of the object R in the first coordinate system may be accurately evaluated.

Examples of a non-transitory computer-readable recording medium storing computer commands to execute the motion evaluation method include magnetic media, e.g., hard disks, floppy disks, and magnetic tapes, optical media, e.g., compact disc read only memories (CD-ROMs) and digital versatile disks (DVDs), magneto-optical media, e.g., floptical disks, and hardware device configured to store and execute program commands, for example, programming modules, e.g., read only memories (ROMs), random access memories (RAMs), flash memories. Also, the program commands may include not only machine codes created by a compiler but also high-level language codes executable by a computer using an interpreter. The above-described hardware apparatuses may be configured to operate as one or more software modules to perform operations according to various embodiments of the present inventive concept, or vise versa.

The computer program may be specially designed and configured for the present inventive concept or may be well-known to one skilled in the art of computer software, to be usable. An example of a computer program may include not only machine codes created by a compiler but also high-level language codes executable by a computer using an interpreter.

The particular implementations shown and described herein are illustrative examples of the inventive concept and are not intended to otherwise limit the scope of the inventive concept in any way. For the sake of brevity, conventional electronics, control systems, software development and other functional aspects of the systems may not be described in detail. Furthermore, the connecting lines, or connectors shown in the various figures presented are intended to represent functional relationships and/or physical or logical couplings between the various elements. It should be noted that many alternative or additional functional relationships, physical connections or logical connections may be present in a practical device. Moreover, no item or component is essential to the practice of the inventive concept unless the element is specifically described as "essential" or "critical."

As described above, according to the motion evaluation system according to the above-described embodiment, an accurate position of an object may be tracked by using the marker member and the cameras, and by converting the position to the first coordinate system corresponding to a treatment room coordinate system, a motion of the object may be accurately evaluated.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A motion evaluation system comprising:
a marker member comprising a body part having a first surface and a second surface parallel to the first surface, a reference indication part indicating, a center of the first surface, and a plurality of markers arranged on the first surface to be spaced apart from the reference indication part, wherein the marker member is arranged on an object such that the reference indication part is arranged at a reference point of a first coordinate system;
a plurality of cameras configured to generate coordinate images by respectively photographing the plurality of markers;
a first coordinate calculator configured to calculate first coordinate values of the plurality of markers in a first coordinate system by using separation distances of the plurality of markers and a first distance between the first surface and the second surface, the separation distances and the first distance being previously stored;
a second coordinate calculator configured to calculate second coordinate values of the plurality of markers in a second coordinate system by using the coordinate images generated by the plurality of cameras; and
a coordinate converter configured to produce a conversion relationship between the first coordinate system and the second coordinate system by using the first coordinate values and the second coordinate values of the plurality of markers, and to convert second motion information in the second coordinate system corresponding to a motion of the object objected by using the plurality of cameras to first motion information in the first coordinate system.

2. The motion evaluation system of claim 1, further comprising a laser member indicating a reference point of the first coordinate system.

3. The motion evaluation system of claim 1, wherein the marker member comprises at least three markers.

4. The motion evaluation system of claim 3, wherein the plurality of markers comprise a first marker, a second marker, a third marker, and a fourth marker arranged on the first surface of the body part.

5. The motion evaluation system of claim 4, wherein the first coordinate calculator calculates a three-dimensional (3D) first coordinate value of the plurality of markers by using the first marker, the second marker, the third marker, and the fourth marker.

6. The motion evaluation system of claim 5, wherein the first coordinate calculator calculates a first-1 coordinate value, a first-2 coordinate value, a first-3 coordinate value, and a first-4 coordinate value respectively corresponding to the first marker, the second marker, the third marker, and the fourth marker and a first-5 coordinate value, a first-6 coordinate value, a first-7 coordinate value, and a first-8 coordinate value at positions respectively corresponding to the first marker, the second marker, the third marker, and the fourth marker on the second surface.

7. The motion evaluation system of claim 6, wherein the second coordinate calculator calculates a 3D second coordinate value of the plurality of markers by using the first marker to the fourth marker.

8. The motion evaluation system of claim 7, wherein the second coordinate calculator calculates a second-1 coordinate value, a second-2 coordinate value, a second-3 coordinate value, and a second-4 coordinate value of the first marker, the second marker, the third marker, and the fourth marker corresponding to the second coordinate system by using the coordinate images generated by the plurality of cameras, and calculates a second-5 coordinate value, a second-6 coordinate value, a second-6 coordinate value, and a second-8 coordinate value on the second surface at positions respectively corresponding to the first marker, the second marker, the third marker, and the fourth marker by using the previously stored separation distances of the plurality of markers and first distance, and the calculated second-1 coordinate value, the calculated second-2 coordinate value, the calculated second-3 coordinate value, and the calculated second-4 coordinate value.

9. The motion evaluation system of claim 8, wherein the coordinate converter produces a conversion matrix that defines a conversion relationship between the first coordinate system and the second coordinate system by generating a first matrix of the first-1 coordinate value, the first-2 coordinate value, the first-3 coordinate value, the first-4 coordinate value, the first-5 coordinate value, the first-6 coordinate value, the first-7 coordinate value, and the first-8 coordinate value, generating a second matrix of the second-1 coordinate value, the second-2 coordinate value, the second-3 coordinate value, the second-4 coordinate value, the second-5 coordinate value, the second-6 coordinate value, the second-7 coordinate value, and the second-8 coordinate value, calculating an inverse matrix of any one of the first matrix and the second matrix, and calculating the inverse matrix and the other one of the first matrix and the second matrix.

10. A motion evaluation method comprising:
preparing a marker member on an object, the marker member comprising a body part having a first surface and a second surface parallel to the first surface, a reference indication part indicating a center of the first surface, and a plurality of markers arranged on the first surface to be spaced apart from the reference indication part;
arranging a center of the first surface of the marker member at a reference point of a first coordinate system;
calculating, by using a first coordinate calculator, first coordinate values of the plurality of markers in a first coordinate system by using separation distances of the plurality of markers and a first distance between the first surface and the second surface, the separation distances and the first distance being previously stored;
generating, by using a plurality of cameras, coordinate images of a plurality of markers by photographing the plurality of markers;
calculating, by using a second coordinate calculator, second coordinate values of the plurality of markers in a second coordinate system by using the coordinate images generated by the plurality of cameras; and
producing a conversion relationship between the first coordinate system and the second coordinate system by using the first coordinate values and the second coordinate values of the plurality of markers.

11. The motion evaluation method of claim 10, further comprising:
converting, by using the coordinate converter, second motion information in the second coordinate system corresponding to a motion of the object objected by using the plurality of cameras, to first motion information in the first coordinate system.

12. The motion evaluation method of claim 10, further comprising:
indicating a reference point of the first coordinate system by using a laser member.

13. The motion evaluation method of claim 10, wherein the marker member comprises at least three markers.

14. The motion evaluation method of claim 13, wherein the plurality of markers comprise a first marker, a second marker, a third marker, and a fourth marker arranged on the first surface of the body part.

15. The motion evaluation method of claim 14, wherein the calculating of the first coordinate value comprises calculating a three-dimensional (3D) first coordinate value of the plurality of markers by using the first marker, the second marker, the third marker, and the fourth marker.

16. The motion evaluation method of claim 15, wherein the calculating of the first coordinate value comprises:
calculating a first-1 coordinate value to a first-4 coordinate value corresponding to the first marker, the second marker, the third marker, and the fourth marker; and
calculating a first-5 coordinate value to a first-8 coordinate value at positions corresponding to the first marker, the second marker, the third marker, and the fourth marker on the second surface of the body part.

17. The motion evaluation method of claim 16, wherein the calculating of the second coordinate valve comprises calculating a 3D second coordinate value of the plurality of markers by using the first marker, the second marker, the third marker, and the fourth marker.

18. The motion evaluation method of claim 17, wherein the calculating of the second coordinate value comprises:
calculating a second-1 coordinate value to a second-4 coordinate value of the first marker to the fourth marker corresponding to the second coordinate system by using the coordinate images; and
calculating a second-5 coordinate value to a second-8 coordinate value on the second surface of the body part at positions corresponding to the first marker to the fourth marker by using the previously stored separation distances of the plurality of markers and first distance, and the calculated second-1 coordinate value to second-4 coordinate value.

19. The motion evaluation method of claim 18, wherein the producing of the conversion relationship comprises;
generating a first matrix of the first-1 coordinate value to the first-8 coordinate value;
generating a second matrix of the second-1 coordinate value to the second-8 coordinate value;
calculating an inverse matrix of any one of the first matrix and the second matrix; and
calculating the inverse matrix and the other one of the first matrix and the second matrix, thereby producing a conversion matrix defining a conversion relationship between the first coordinate system and the second coordinate system.

20. A non-transitory computer readable recording medium having recorded thereon a program, which when executed by a computer, performs the method of claim 10.

* * * * *